(12) United States Patent
Yoshino

(10) Patent No.: US 9,254,084 B2
(45) Date of Patent: Feb. 9, 2016

(54) FUNDUS PHOTOGRAPHING APPARATUS

(71) Applicant: NIDEK CO., LTD., Gamagori-shi, Aichi (JP)

(72) Inventor: Masayuki Yoshino, Gamagori (JP)

(73) Assignee: NIDEK CO., LTD., Gamagori-shi (JP)

( * ) Notice: Subject to any disclaimer, the term of this patent is extended or adjusted under 35 U.S.C. 154(b) by 22 days.

(21) Appl. No.: 13/921,666

(22) Filed: Jun. 19, 2013

(65) Prior Publication Data

US 2014/0002795 A1 Jan. 2, 2014

(30) Foreign Application Priority Data

Jun. 29, 2012 (JP) ................................. 2012-146238

(51) Int. Cl.
*A61B 3/14* (2006.01)
*A61B 3/12* (2006.01)

(52) U.S. Cl.
CPC .... *A61B 3/14* (2013.01); *A61B 3/12* (2013.01)

(58) Field of Classification Search
CPC ...... A61B 3/12; A61B 3/0008; A61B 3/1005; A61B 3/14; A61B 3/10; A61B 3/145; A61B 3/156; G06T 2207/30041; G06T 2207/10048
USPC ......... 351/205, 206, 208, 214, 221, 243, 246; 348/78
See application file for complete search history.

(56) References Cited

U.S. PATENT DOCUMENTS

| | | | |
|---|---|---|---|
| 4,265,518 A | | 5/1981 | Matsumura |
| 5,141,302 A * | | 8/1992 | Arai et al. ..................... 351/205 |
| 7,445,336 B2 * | | 11/2008 | Ichikawa ..................... 351/206 |
| 7,506,982 B2 * | | 3/2009 | Yahagi et al. ................. 351/206 |
| 8,061,840 B2 * | | 11/2011 | Mizuochi ..................... 351/206 |
| 2005/0068496 A1 * | | 3/2005 | Ichikawa ..................... 351/206 |
| 2005/0068497 A1 * | | 3/2005 | Hanebuchi et al. ........... 351/206 |
| 2006/0176447 A1 * | | 8/2006 | Reis .......................... A61B 3/12 351/214 |
| 2006/0232683 A1 | | 10/2006 | Ichihashi |
| 2009/0303439 A1 * | | 12/2009 | Kawai .......................... 351/211 |
| 2012/0026461 A1 * | | 2/2012 | Chou et al. .................... 351/206 |
| 2012/0050515 A1 * | | 3/2012 | Shikaumi et al. ............... 348/78 |
| 2013/0128226 A1 * | | 5/2013 | Yahagi et al. ................. 351/206 |
| 2013/0208243 A1 * | | 8/2013 | Sakagawa .................... 351/211 |
| 2013/0222763 A1 * | | 8/2013 | Bublitz .................... A61B 3/12 351/206 |

FOREIGN PATENT DOCUMENTS

| | | | |
|---|---|---|---|
| EP | 1 906 495 A1 | | 4/2008 |
| JP | A-64-058238 | | 3/1989 |
| JP | B2-3243272 | | 10/2001 |

* cited by examiner

OTHER PUBLICATIONS

Oct. 15, 2013 European Search Report issued in European Patent Application No. 13173094.7.

*Primary Examiner* — Bumsuk Won
*Assistant Examiner* — Collin X Beatty
(74) *Attorney, Agent, or Firm* — Oliff PLC

(57) ABSTRACT

A fundus photographing apparatus includes: an illumination optical system for illuminating a fundus of a examinee's eye; and a photographing optical system for photographing the fundus illuminated by the illumination optical system. The photographing optical system includes: a first aperture diaphragm for forming an image of the aperture diaphragm in a position between a pupil and a posterior surface of a crystalline lens of the eye; and a second aperture diaphragm for forming an image of the aperture diaphragm not acting as a field diaphragm, in a position between the fundus of the eye and the image of the first aperture diaphragm.

7 Claims, 10 Drawing Sheets

Normal Photographing Mode     Small Pupil Eye Photographing Mode

Normal Photographing Mode     Small Pupil Eye Photographing Mode

Normal Photographing Mode     Small Pupil Eye Photographing Mode

US 9,254,084 B2

FUNDUS PHOTOGRAPHING APPARATUS

CROSS-REFERENCE TO RELATED APPLICATIONS

This application is based upon and claims the benefit of priority from the prior Japanese Patent Application No. 2012-146238, filed Jun. 29, 2012, the entire contents of which are incorporated herein by reference.

BACKGROUND OF THE INVENTION

1. Field of the Invention

The present invention relates to a fundus photographing apparatus for photographing a fundus of an examinee's eye.

2. Related Art

In a case where a conventional fundus camera photographs an examinee's eye with a small pupil, this small or contracted pupil blocks a region of ring-shaped illumination light near its outer edge. Thus, a central area of a photographed or captured image is insufficiently illuminated and darkened. To avoid such insufficient illumination (brightness) at the central area of the photographed image, there is a known technique in which when an examinee's eye with a small pupil is to be photographed, the size of a light shielding plate of an illumination optical system is changed according to the size of a pupil diameter of the examinee's eye (see Patent Document 1). If the size of a light shielding plate is changed according to a small pupil diameter, the problem with insufficient illumination is minimized but flare is apt to superimpose the peripheral edge of the photographed image. To avoid such a defective, another known technique is arranged to narrow an illumination range of a fundus (see Patent Document 2).

RELATED ART DOCUMENTS

Patent Documents

Patent Document 1: JP 64(1989)-58238A
Patent Document 2: JP5(1993)-199997A (JP 3243272B2)

SUMMARY OF INVENTION

Problems to be Solved by the Invention

However, according to the technique disclosed in Patent Document 2 arranged to narrow the illumination range, a photographing field angle (angle of view) is substantially narrowed. Fundus abnormality is likely to advance in a peripheral portion of the photographing field angle. Due to the narrowed illumination range, information of the fundus is apt to be lost. A fundus camera used in screening is often designed with a photographing field angle of 45° which is unambiguously determined and put into practice. In the above usage environment, the field angle is insufficient.

The present invention has been made in view of the circumstances and has a purpose to provide a fundus photographing apparatus capable of providing a suitable photographing field angle and obtaining a fundus image with less flare.

Means of Solving the Problems

To achieve the above purpose, one aspect of the invention provides a fundus photographing apparatus including: an illumination optical system for illuminating a fundus of a examinee's eye; and a photographing optical system for photographing the fundus illuminated by the illumination optical system, wherein the photographing optical system includes: a first aperture diaphragm for forming an image of the aperture diaphragm in a position between a pupil and a posterior surface of a crystalline lens of the eye; and a second aperture diaphragm for forming an image of the aperture diaphragm not acting as a field diaphragm, in a position between the fundus of the eye and the image of the first aperture diaphragm.

Effects of the Invention

According to the present invention, even when a fundus photographing apparatus photographs a fundus of an examinee's eye with a small pupil diameter, a fundus image with less loss of fundus information can be obtained.

DESCRIPTION OF EMBODIMENTS

Figure 1:
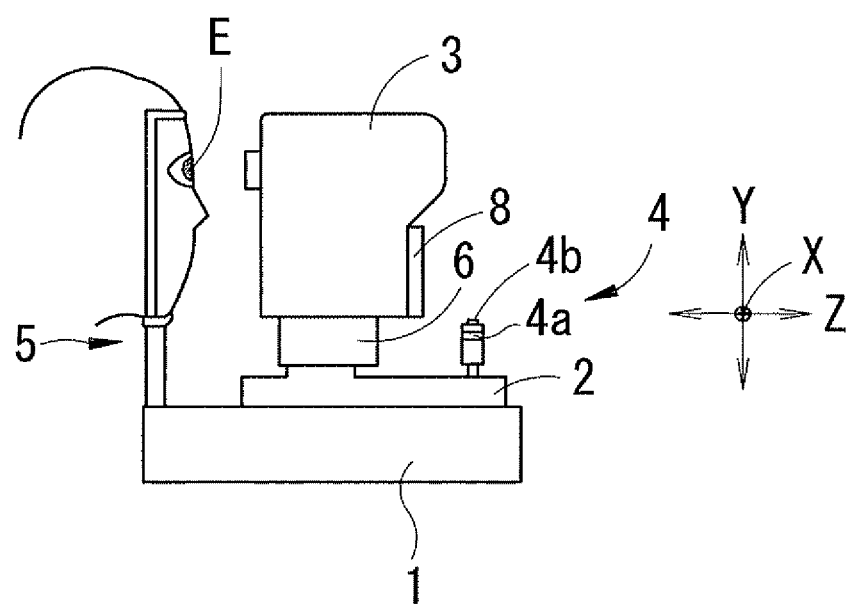
FIG. 1 is a schematic external view of a fundus camera in an embodiment.

A detailed description of a preferred embodiment of the present invention will now be given referring to the accompanying drawings. FIG. 1 is a schematic external view of a fundus camera in the present embodiment. This fundus camera includes a base 1, a movable table 2 configured to be movable relative to the base 1 in a right and left direction (X direction) and a back and forth (working distance) direction (Z direction), a photographing unit (a main unit) 3 provided to be movable in three-dimensional directions relative to the movable table 2 and contain an optical system mentioned later, and a head supporting unit 5 fixed to the base 1 to support the face (head) of an examinee.

The fundus camera further includes an automatic moving mechanism provided with an electric motor and arranged to relatively move the photographing unit 3 with respect to an eye E of the examinee. To be concrete, the photographing unit 3 is moved in the right and left direction (X direction), up and down direction (Y direction), and back and forth direction (Z direction) to the eye E by an XYZ drive unit 6 provided in the table 2 and to be electrically powered. In the fundus camera, a manual moving mechanism is also provided to relatively move the photographing unit 3 to the eye E by operation of an operating member (a joystick 4). To be concrete, a sliding mechanism not shown is provided to slide the movable table 2 on the base 1. By operation of the joystick 4, the table 2 is slid in the XY directions on the base 1. By operation of a rotation knob 4a, the XYZ drive unit 6 is Y-driven to move the photographing unit 3 in the up and down direction. On an examiner side of the photographing unit 3, a monitor 8 is provided to display a fundus observation image, a fundus photographing image, an anterior segment observation image, and others.

Figure 2A:
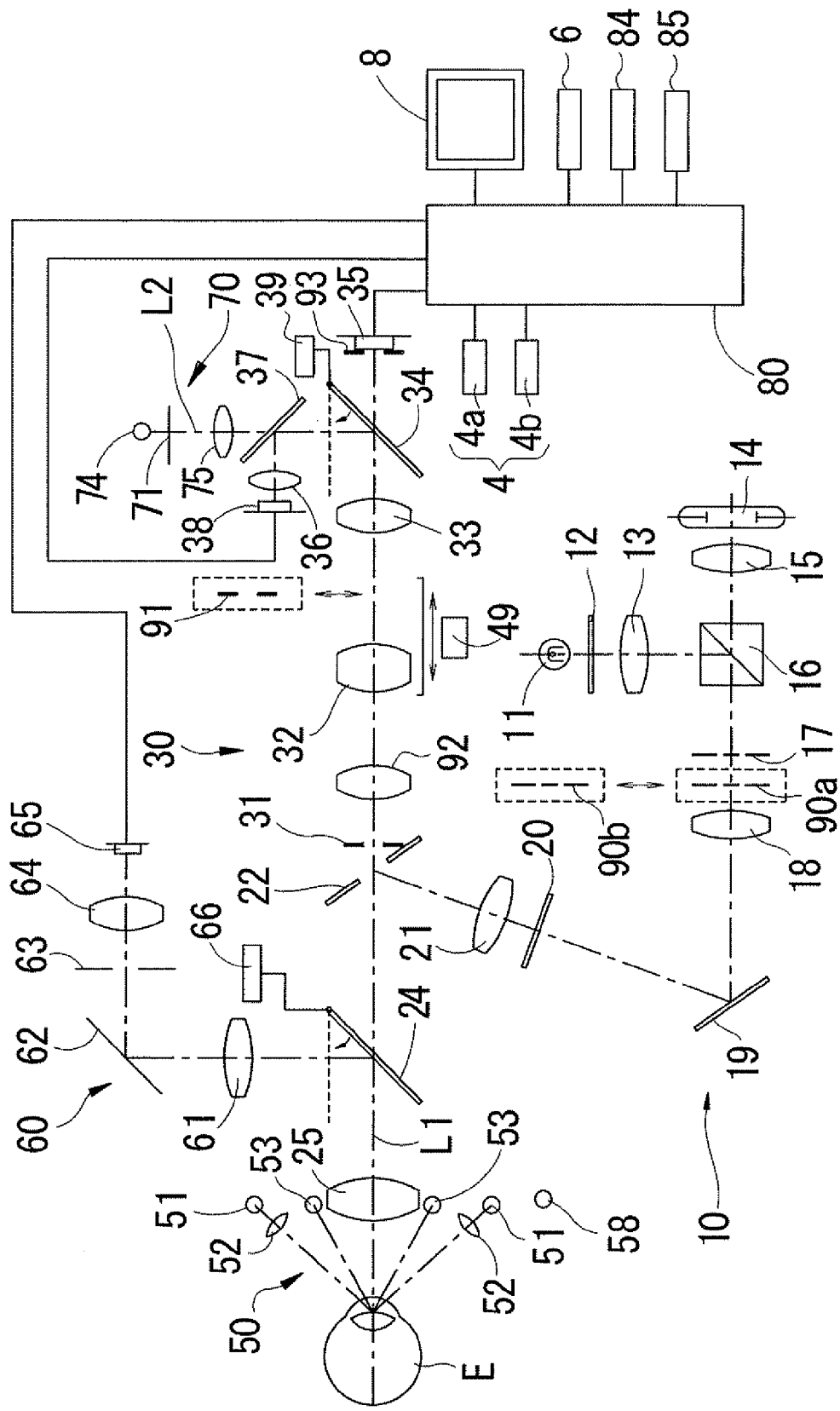
FIG. 2A is a diagram showing optical systems and a control system of the fundus camera in the embodiment.
Figure 2B:
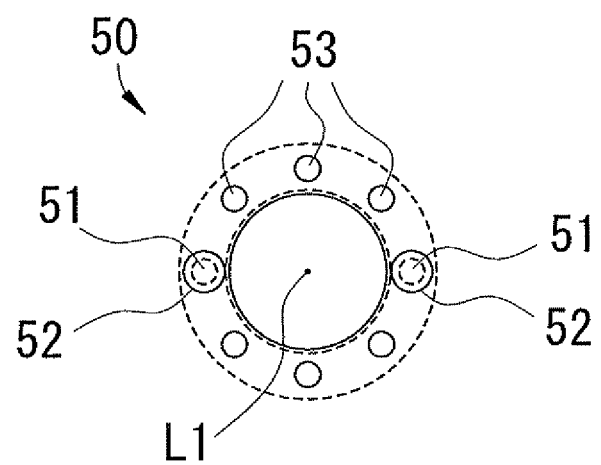
FIG. 2B is an enlarged diagram showing an alignment mark projecting optical system seen in an optical axis direction.

FIG. 2A is a schematic configuration view of the optical systems and the control system contained in the photographing unit 3. FIG. 2B is an enlarged diagram showing an alignment mark projecting optical system seen in an optical axis direction. In FIG. 2A, the optical systems roughly include an illumination optical system 10, a fundus observing and photographing optical system 30 to photograph a fundus image of an examinee's eye E, an alignment mark projecting optical system 50, an anterior segment observing optical system 60, and a fixation target presenting optical system 70.

<Illumination Optical System>

The illumination optical system 10 includes an observing illumination optical system and a photographing illumination optical system. The photographing illumination optical system includes a photographing light source 14 such as a flash lamp, a condenser lens 15, a ring slit 17, a light shielding plate 90a (90b), a relay lens 18, a mirror 19, a black point plate 20 having a black point at a center, a relay lens 21, a perforated mirror 22, and an objective lens 25. The light shielding plate 90a and the light shielding plate 90b used in the present embodiment are each formed with a ring-shaped aperture and are selectable to be placed in a substantially conjugated position with a posterior surface of a crystalline lens of the eye E in an optical path of the illumination optical system 10. The light shielding plate 90a and the light shielding plate 90b are different in aperture inner diameter. The light shielding plate 90a is used for an examinee's eye having a pupil diameter enough for a normal photographing mode. The light shielding plate 90b is used for an examinee's eye having a pupil diameter insufficient for photographing, that is, a so-called small pupil diameter. In the present embodiment, therefore, an open region of the light shielding plate 90a is smaller than an open region of the light shielding plate 90b. The observing illumination optical system includes a light source 11 such as a halogen lamp, an infrared filter 12 allowing near infrared light having a wavelength of 750 nm or more to pass therethrough, a condenser lens 13, a dichroic mirror 16, and an optical system from the ring slit 17 to the objective lens 25. The dichroic mirror 16 has the property of reflecting infrared light emitted from the light source 11 while transmitting visible light emitted from the photographing light source 14.

<Fundus Observing and Fundus Photographing Optical System>

The fundus observing and photographing optical system 30 includes the objective lens 25, a photographing diaphragm 31 located near an aperture of the perforated mirror 22, an image forming lens 92, a focusing lens 32 movable in the optical axis direction, an aperture diaphragm 91, an image forming lens 33, and a flip-up mirror 34 that is inserted in and removed from an optical path by an inserting/removing mechanism 39 during fundus photographing. The aperture diaphragm 91 is removably placed in a substantially conjugated position with a crystalline lens of the eye E in an optical path of the photographing optical system 30. In the present embodiment, the aperture diaphragm 91 is inserted in the optical path of the photographing optical system at the same time when the light shielding plate 90b is inserted in the optical path of the illumination optical system 10. In the present embodiment, furthermore, an optical system to establish a substantial conjugate relationship between the aperture diaphragm 91 and the crystalline lens of the eye E is configured as an infinity correction optical system. The photographing optical system and the fundus observing optical system share the objective lens 25 and an optical system from the photographing diaphragm 31 to the image forming lens 33. The photographing diaphragm 31 is placed in a substantially conjugated position with a pupil of the eye E through the objective lens 25. The focusing lens 32 and the aperture diaphragm 91 are moved in the optical axis direction by a moving mechanism 49 having a motor. In the present embodiment having the infinity correction optical system, it is possible to move the focusing lens 32 and the aperture diaphragm 91 along the optical axis while keeping a positional relationship between the focusing lens 32 and the aperture diaphragm 91. Accordingly, even when the focusing lens 32 is moved for focus adjustment according to a diopter of the eye E, the size and the position of the aperture diaphragm 91 located in the substantial conjugated position with the crystalline lens of the eye E through the objective lens 25 remains unchanged. A two-dimensional imaging element 35 used in photographing is sensitive to a visible region and a field diaphragm 93 is placed immediately in front of and in close contact with the imaging element 35. In an optical path in a reflection direction from the flip-up mirror 34, there are arranged a dichroic mirror 37 having the property of reflecting infrared light and transmitting visible light, a relay lens 36, and an imaging element 38 (a two-dimensional imaging element) for observation having a sensitivity to an infrared region.

Between the objective lens 25 and the perforated mirror 22, a dichroic mirror (a wavelength selecting mirror) 24 serving as an optical path splitting member is obliquely placed to be inserted/removed. This dichroic mirror 24 has the property of reflecting wavelength light (Center wavelength: 940 nm) of the alignment mark projecting optical system 50 and the anterior segment illumination light source 58, while transmitting a wavelength of 900 nm or less including a light source wavelength (Center wavelength: 880 nm) of wavelength light of the fundus observing illumination. During photographing, the dichroic mirror 24 is flipped up by the inserting/removing mechanism 66 in sync with the flip-up mirror 34 and retracted out of the optical path. The inserting/removing mechanism 66 may consist of a solenoid, a cam, and others.

Light emitted from the observation light source 11 is converted to infrared light by the infrared filter 12, passing through the condenser lens 13, and then is reflected by the dichroic mirror 16 to illuminate the ring slit 17. The light passing through the ring slit 17 passes through the relay lens 18, the mirror 19, the black point plate 20, and the relay lens 21 and falls on the perforated mirror 22. The light reflected by the perforated mirror 22 passes through the dichroic mirror 24 and converges once on a point near the pupil of the eye E by the objective lens 25 and then disperses to illuminate the fundus of the eye E.

The reflection light from the fundus passes through the objective lens 25, the dichroic mirror 24, the aperture of the perforated mirror 22, the photographing diaphragm 31, the focusing lens 32, the aperture diaphragm 91, the image forming lens 33, the flip-up mirror 34, the dichroic mirror 37, and the relay lens 36, and finally forms an image on the imaging element 38. Output of the imaging element 38 is inputted to a controller 80. The monitor 8 displays a fundus observation image of the eye E captured by the imaging element 38. The light from the photographing light source 14 passes through the condenser lens 15 and the dichroic mirror 16 and then travels along the same optical path as the illumination light for fundus observation. Thus, the fundus is illuminated with visible light. The reflection light from the fundus passes through the objective lens 25, the aperture of the perforated mirror 22, the photographing diaphragm 31, the focusing lens 32, and the image forming lens 33 and then forms an image on the two-dimensional imaging element 35.

<Alignment Mark Projecting Optical System>

The alignment mark projecting optical system 50 for projecting mark light for alignment includes a plurality of infrared light sources concentrically arranged at angular intervals of 45° about the photographing optical axis L1 as shown in FIG. 2B. Specifically, this optical system 50 further includes a first mark projecting optical system (0° and 180°) having two pairs of infrared light sources 51 and collimating lenses 52, the pairs being placed in right and left symmetric relation with respect to a vertical plane passing the photographing optical axis L1, and a second mark projecting optical system having six infrared light sources 53 arranged in positions different from the first mark projecting optical system. In this case, the first mark projecting optical system is configured to project infinite marks from right and left directions onto the cornea of the eye E and the second mark projecting optical system is configured to project finite marks from up and down directions or oblique directions onto the cornea of the eye E. In FIG. 2A, for convenience, the first mark projecting optical system (0° and 180°) and only a part of the second mark projecting optical system (45° and 135°) are illustrated.

<Anterior Segment Observing Optical System>

The anterior segment observing (photographing) optical system 60 for imaging an anterior segment of the examinee's eye includes, on a reflecting side of the dichroic mirror 24, a field lens 61, a mirror 62, a diaphragm 63, a relay lens 64, and a two-dimensional imaging element (light receiving element) 65 having a sensitivity to an infrared region. The two-dimensional imaging element 65 is also used as an imaging means for detecting alignment marks, whereby images the anterior segment illuminated by the anterior-segment illumination light source 58 that emits infrared light having a center wavelength of 940 nm and the alignment mark. The light from the anterior segment illuminated by the light source 58 passes through the objective lens 25, the dichroic mirror 24, and the optical system from the field lens 61 to the relay lens 64 and then falls on the two-dimensional imaging element 65. Furthermore, alignment light emitted from the light source of the alignment mark projecting optical system 50 is projected to the cornea of the eye E and a corneal reflection image is received by (projected to) the two-dimensional imaging element 65 via the objective lens 35 to the relay lens 64. Output of the two-dimensional imaging element 65 is inputted to the controller 80 and the monitor 8 displays an anterior segment image captured by the two-dimensional imaging element 65. The anterior-segment observing optical system 60 also uses an alignment detecting optical system having a light receiving element (the two-dimensional imaging element 65) to detect misalignment (alignment deviation) of the photographing unit 3 with respect to the examinee's eye E.

<Fixation Target Presenting Optical System>

The fixation target presenting optical system 70 for presenting a fixation target to induce the examinee's eye E to hold fixation includes a red light source 74, a light shielding plate 71 formed with a hole, and a relay lens 75, and further shares the optical path of the fundus observing and photographing optical system 30 from the flip-up mirror 34 to the objective lens 25 through the dichroic mirror 37. The fixation target presenting optical system 70 has a configuration (not shown) to change a presenting position of a fixation target, whereby directing the visual line of the eye E in a predetermined direction (e.g., see JP 2005-95450A). Accordingly, peripheral photographing can also be performed. In this case, the light shielding plate 71 illuminated from behind by the light source 74 and forms a fixation target (a fixation lamp). The light from the fixation target passes through the relay lens 75, the dichroic mirror 37, the flip-up mirror 34, the image forming lens 33, the focusing lens 32, the perforated mirror 22, the dichroic mirror 24, and the objective lens 25, and then converges on the fundus of the eye E. At that time, the examinee visually recognizes, as the fixation target, the light from the light shielding plate 71 formed with the hole.

<Control System>

The two-dimensional imaging elements 65, 38, and 35 are connected to the controller 80. This controller 80 detects alignment marks from the anterior segment image captured by the two-dimensional imaging element 65 and processes the detected marks. The controller 80 is also connected to the monitor 8 to control an image displayed thereon. To the controller 80, furthermore, there are connected the XYZ drive unit 6, the moving mechanism 49, the inserting/removing mechanism 39, the rotation knob 4a, photographing switch 4b, a switch unit 84 having various switches, a memory 85 serving as a storage means, each light source, and others. Herein, the controller 80 detects misalignment of the photographing unit 3 with respect to the examinee's eye E based on a light receiving signal outputted from the imaging element (light receiving element) 65 and, based on this detection result, outputs a drive signal to the XYZ drive unit 6.

Figure 3A:
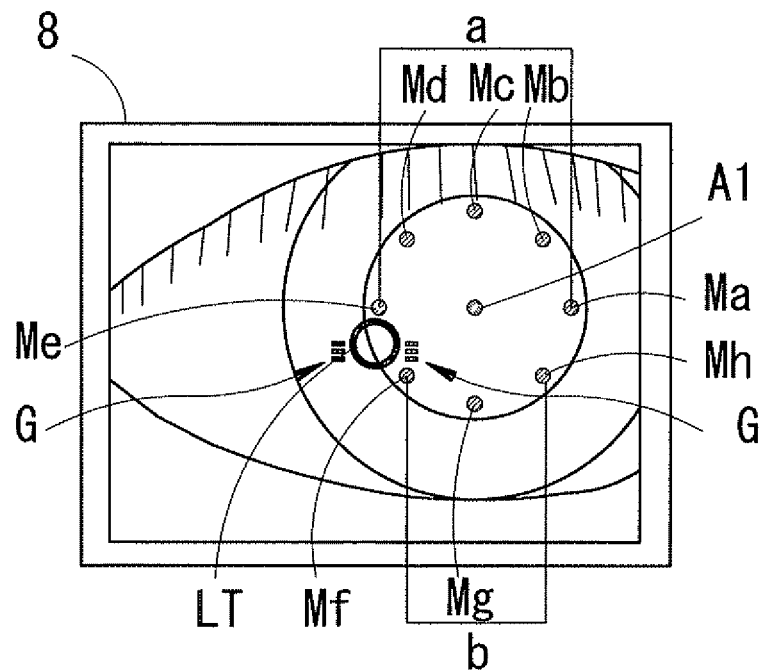
FIGS. 3A and 3B are diagrams showing alignment to an anterior segment image displayed on a monitor.
Figure 3B:
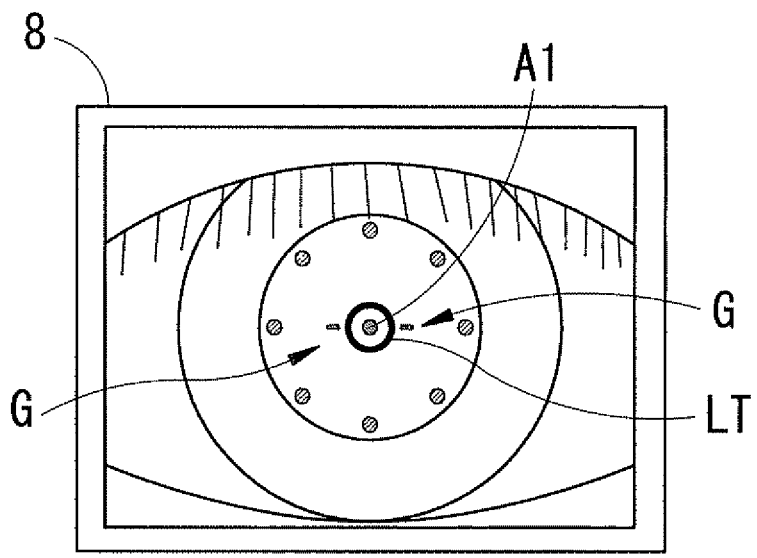
Figure 4:
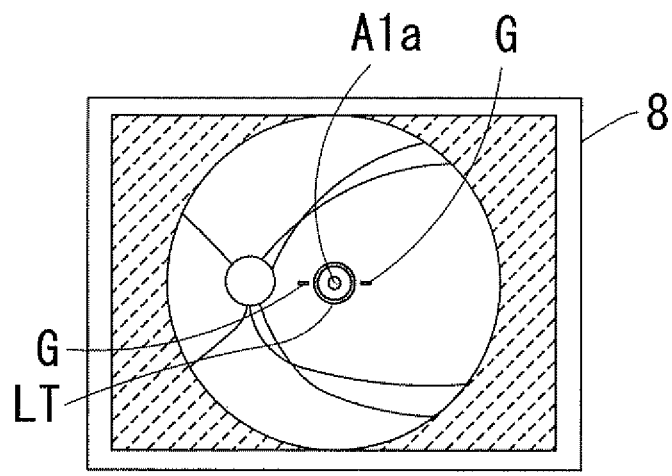
FIG. 4 is a diagram showing a displayed state of a fundus image on the monitor.
Figure 5:
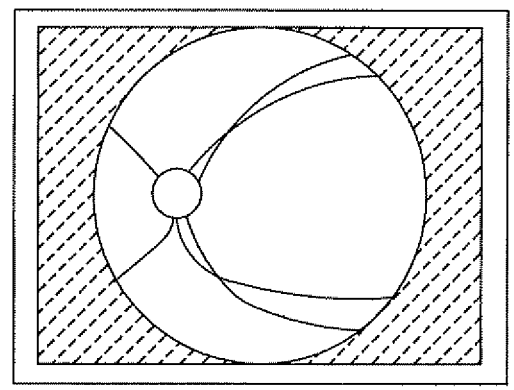
FIG. 5 is a diagram showing a displayed state of a photographed fundus image on the monitor.

The controller 80 electronically creates and displays a reticle (an alignment mark) LT serving as an alignment reference at a predetermined position on a screen of the monitor 8 as shown in anterior-segment image observation screens of FIGS. 3A and 3B and a fundus observation screen of FIG. 4. Furthermore, the controller 80 electronically creates and displays an alignment mark A1 on the screen of the monitor 8 so that a relative distance between the alignment mark A1 and the reticle LT changes based on the detected misalignment in the XY directions. The controller 80 further displays indicators G representing the misalignment in the Z direction and increases/decreases the number of bars constituting each indicator G based on the detected misalignment in the Z direction. In the present embodiment, an alignment completion position (an alignment reference position) of the photographing unit 3 with respect to the eye E in the Z direction is changed depending on the position of the photographing optical axis (optical axis L1) of the photographing unit 3 with respect to the eye E. In the present embodiment, accordingly, the alignment completion position in the Z direction is changed according to the misalignment in the XY directions, Operations of the fundus camera configured as above will be explained below. The following explanation is given to an example of photographing of an examinee's eye E with a small pupil.

When powered on, the controller 80 executes operations of initializing a presenting position of a fixation target, an alignment reference position, a reticle display position, and others. The fixation target presenting position can be changed with a predetermined switch for changing a visual line direction provided in the switch unit 84.

An examiner first asks an examinee to put his/her head on the head supporting unit 5. In an initial stage, the dichroic mirror 24 is placed in the optical path of the photographing optical system 30 and an anterior segment image captured by the two-dimensional imaging element 65 is displayed on the monitor 8. The examiner operates the joystick 4 to move the photographing unit 3 in right, left, up, and down directions so that the anterior segment image appears on the monitor 8. When the anterior segment image appears on the monitor 8, eight mark images Ma to Mh come to appear as shown in FIG. 3A.

When the alignment mark images projected on the cornea of the eye E are detected by the two-dimensional imaging element 65 as described above, the controller 80 starts automatic alignment control. Herein, the controller 80 detects the misalignment of the photographing unit 3 with respect to the eye E based on an imaging signal from the two-dimensional imaging element 65. The controller 80 electronically displays the reticle LT at a predetermined position (at the center of the monitor 8 in the present embodiment) on the monitor 8 in correspondence with the photographing optical axis L1. The controller 80 detects an approximate corneal vertex position in the form of an XY coordinate of the center of the ring shape formed by the mark images Ma to Mh projected in a ring form and electronically forms the alignment mark A1 at the corresponding position on the monitor 8. To bring the photographing unit 3 in a predetermined relationship with the examinee's eye E, the controller 80 determines a deviation amount between the detected corneal vertex position and the alignment reference position (e.g., an intersection point of an imaging plane of the imaging element 65 and the photographing optical axis L1) in the XY directions set in advance on the imaging element 65. The controller 80 then performs automatic alignment by driving and controlling the XYZ drive unit 6 so that the above deviation amount falls within a permissible range of alignment completion in the XY directions (i.e., so that the reticle LT and the alignment mark A1 coincide with each other).

The controller 80 determines the alignment deviation amount (displacement amount) in the Z direction by comparing an image ratio (a/b) of an image interval "a" between the infinite mark images Ma and Me detected as above and an image interval "b" between the finite mark images Mh and Mf detected as above and an image ratio corresponding to the alignment completion position set in advance in the memory 85. As the alignment completion position in the Z direction (working distance), the controller 80 appropriately retrieves, from the memory 85, a value of the image ratio corresponding to the alignment completion position in the direction corresponding to the deviation amount (displacement amount) in the XY directions of the photographing optical axis L1 from the corneal vertex, and sets the retrieved value as an alignment reference value. Regarding the Z direction, the controller 80 also determines the deviation amount from the alignment completion position in the Z direction and then performs the automatic alignment by driving and controlling the XYZ drive unit 6 so that the deviation amount falls within a permissible range of the set alignment completion position. Based on the alignment deviation amount in the Z direction, the controller 80 electronically displays the indicators G representing an alignment state in the Z direction the on right and left sides of the reticle LT displayed on the monitor 8. The number of bars constituting each indicator G is increased and decreased according to the alignment deviation amount in the Z direction. In the present embodiment, when the alignment deviation amount in the XYZ directions falls within a permissible range, the controller 80 stops driving the XYZ drive unit 6 and also outputs an alignment completion signal and displays the indicators G each consisting of a single bar on the right and left sides respectively (see FIG. 3B).

Herein, the pupil diameter of the eye E is detected by the two-dimensional imaging element 65 and the controller 80. If the pupil diameter is smaller than a predetermined value (e.g., a 4-mm diameter), the light shielding plate 90a used for the normal photographing mode in which the pupil diameter of the eye E is sufficiently wide is changed over to the light shielding plate 90b having a smaller light shielding region than the light shielding plate 90a, and also the aperture diaphragm 91 is inserted in the fundus observing and photographing optical system 30 by an actuator not shown to narrow the photographing light. In the present embodiment, changeover to the light shielding plate 90b and insertion of the aperture diaphragm 91 in the optical path are electrically controlled. However, the invention is not limited thereto. At least one of the light shielding plate 90b and the aperture diaphragm 91 may be manually inserted in the optical path.

Figure 6A:
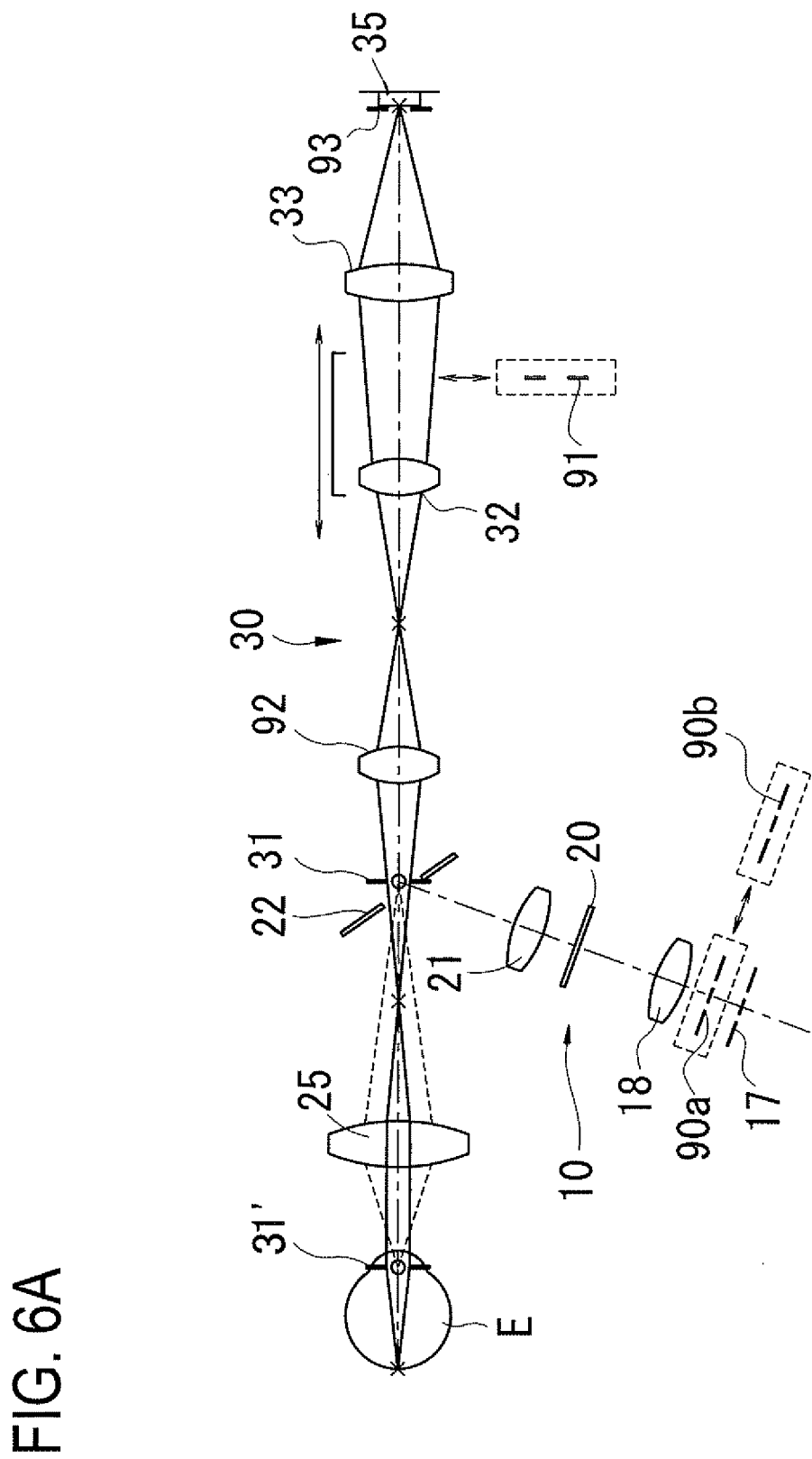
FIG. 6A is a schematic diagram showing a light beam of a fundus observing and photographing optical system.
Figure 6B:
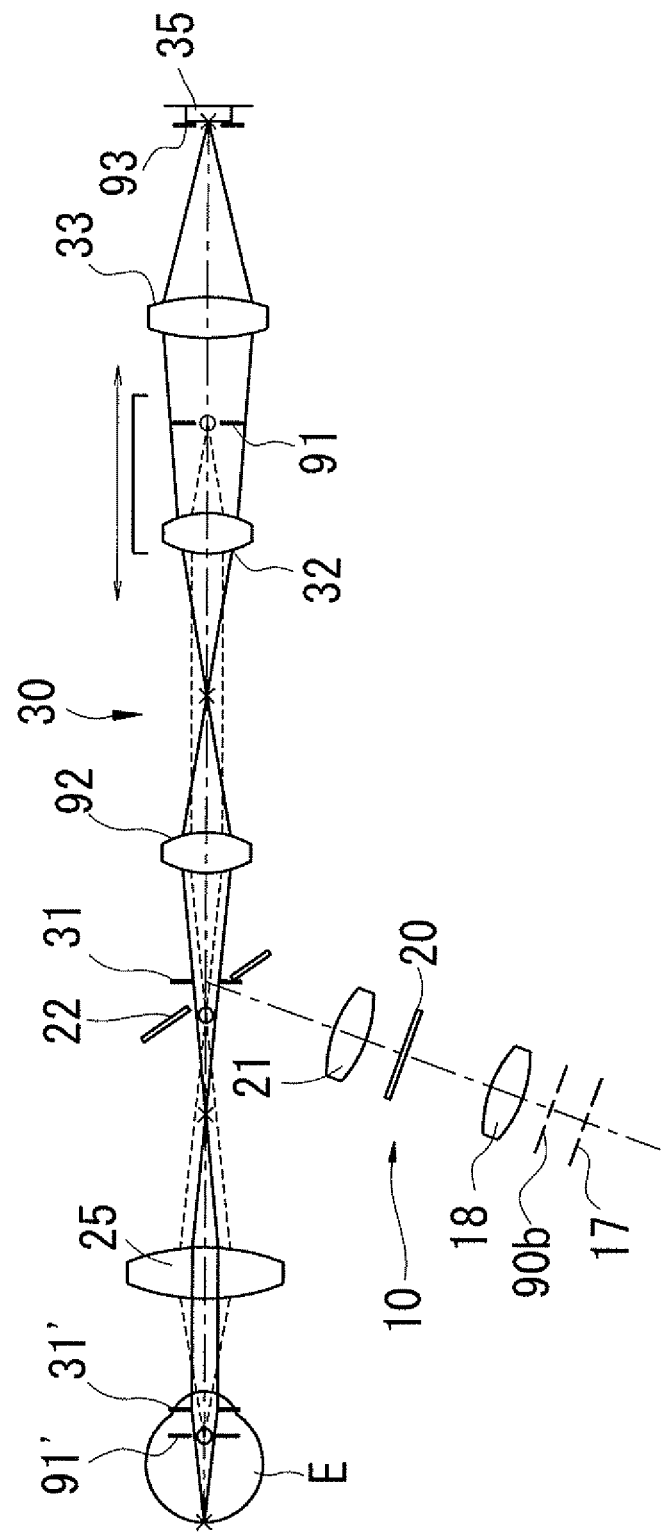
FIG. 6B is another schematic diagram showing a light beam of the fundus observing and photographing optical system.

Herein, image forming relations between the examinee's eye E and the photographing diaphragm 31 and between the eye E and the aperture diaphragm 91 are explained referring to the optical paths illustrated in FIGS. 6A and 6B. In FIG. 6A, broken lines show the image forming relation between the photographing diaphragm 31 conjugated with the pupil of the eye E through the objective lens 25 and its image 31'. In FIG. 6B, broken lines show the image forming relation between the aperture diaphragm 91 conjugated with the crystalline lens of the eye E through the objective lens 25 and its image 91'. The image forming lens 92 and the focusing lens 32 are arranged so that respective lens focus points coincide with a conjugated position of the crystalline lens as shown in FIG. 6B and the light between the lenses 92 and 32 is parallel, forming an infinity correction optical system. Accordingly, even when the focusing lens 32 is moved on the optical axis according to a diopter of the eye E, the distance between the focusing lens 32 and the crystalline lens conjugated position remains unchanged.

When a changeover switch not shown is turned on, the controller 80 causes the monitor 8 to change the anterior segment observation image to the fundus observation image shown in FIG. 4 and completes focus adjustment by using a split mark not shown. Upon depression of the photographing switch 4b, based on its trigger signal, the controller 80 moves the dichroic mirror 24 and the flip-up mirror 34 out of the optical path and turns on the photographing light source 14 to irradiate flash light to the fundus. The reflection light from the fundus is received by the two-dimensional imaging element 35 and a fundus image is thus obtained.

Figure 7A:
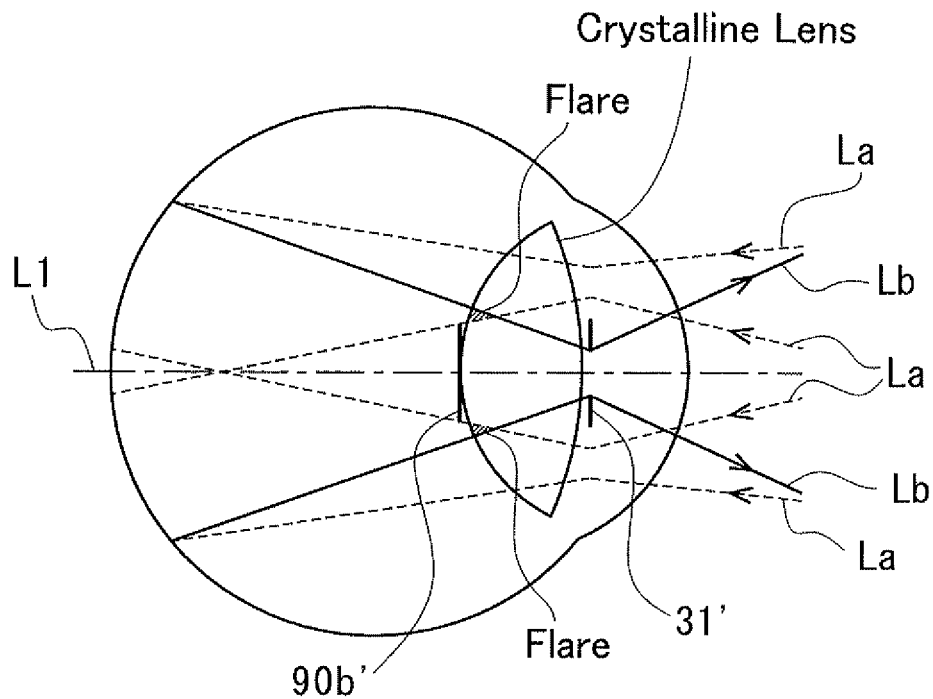
FIGS. 7A and 7B are schematic diagrams showing an illumination light area and a photographing light area of the fundus camera to an examinee's eye.

Herein, the conventional art in which the aperture diaphragm 91 is not inserted in the fundus observing and photographing optical system and flare is superimposed on a peripheral portion of a photographed image is explained referring to a schematic optical path diagram of FIG. 7A. The present embodiment in which the aperture diaphragm 91 is inserted in the fundus observing and photographing optical system and flare is reduced on the peripheral portion of a photographed image is explained referring to a schematic optical path diagram of FIG. 7B. In those diagrams, L1 represents an optical axis, an illumination light beam La is indicated by broken lines and a photographing light beam Lb is indicated by solid lines. As illustrated, the image 31' of the photographing diaphragm 31 is placed near the pupil, and the image 90b' of the light shielding plate 90b is placed on a posterior surface of the crystalline lens. Further, the image 91' of the aperture diaphragm 91 is placed inside the crystalline lens as shown in FIG. 7B.

As described above, FIG. 7A illustrates the conventional art in which the aperture diaphragm 91 is not inserted in the fundus observing and photographing optical system, showing a state where the light shielding plate 90b having a lower light shielding amount suitable for photographing a small pupil is inserted in the optical path. Herein, such an overlapping area as indicated by oblique lines is formed in the crystalline lens by overlapping of the illumination light beam La and the photographing light beam Lb. Accordingly, a part of scattered light of the illumination light generated in the crystalline lens is taken in the photographing light beam Lb. The area defined by the illumination light beam La and the photographing light beam Lb overlapping with each other in the crystalline lens becomes a light beam of a peripheral field angle and hence flare comes out on the peripheral portion of a photographed image. Since the flare is superimposed on fundus information, the fundus information is lost due to the flare.

Figure 7B:
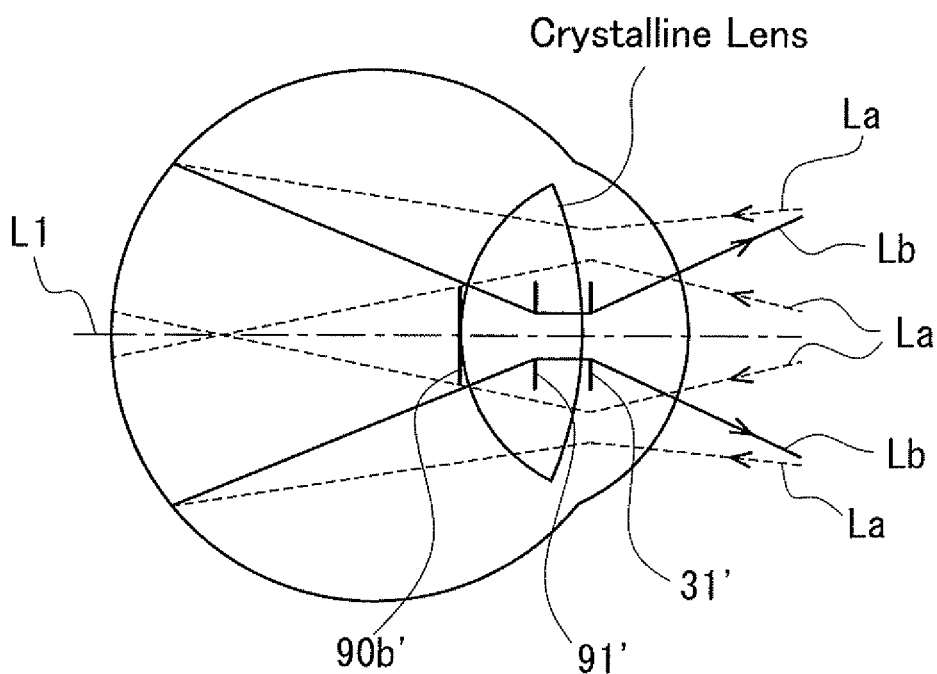

Next, the advantageous effects of the present embodiment in which the aperture diaphragm 91 is inserted in the fundus observing and photographing optical system are explained referring to FIG. 7B. In the crystalline lens, the image 91' of the aperture diaphragm 91 inserted in the fundus observing and photographing optical system 30 is formed through the objective lens 25. The image 91' of the aperture diaphragm 91 applies a limitation to the outer diameter of the photographing light beam Lb between the fundus and the image 31' of the photographing diaphragm 31. In FIG. 7B, as a result, the area indicated by oblique lines in FIG. 7A and caused by overlapping of the illumination light beam La and the photographing light beam Lb is not generated in the crystalline lens. Accordingly, flare is not superimposed on the peripheral portion of a photographed image. This makes it possible to obtain a fundus image without loss of the fundus information.

Figure 8:
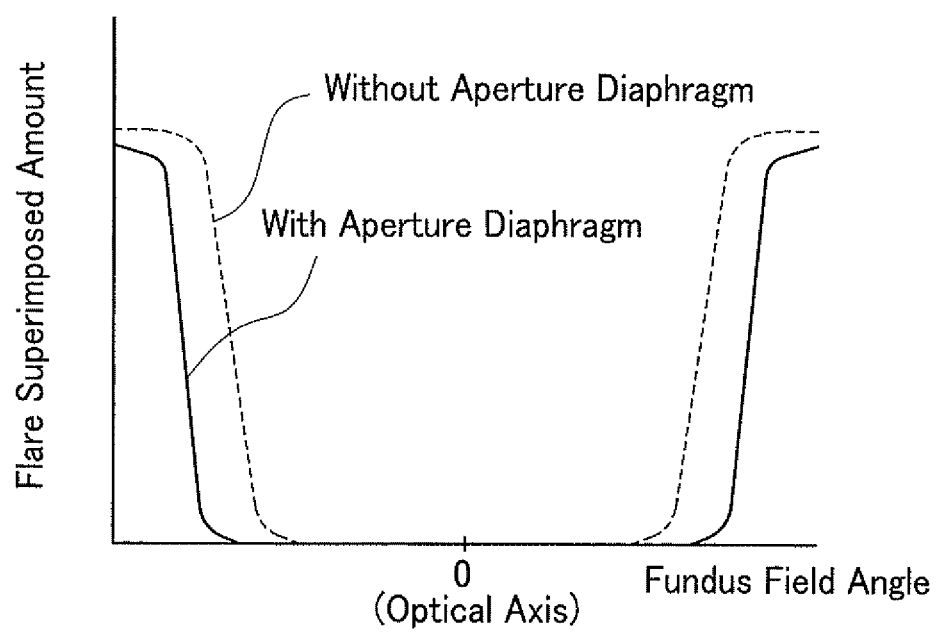
FIG. 8 is a graph showing insertion of an aperture diaphragm and an effect of reducing flare.

Furthermore, a difference between the conventional art where the aperture diaphragm 91 is not inserted in the optical path and the present embodiment where the aperture diaphragm 91 is inserted in the optical path is explained in terms of characteristics of the fundus field angle and the flare superimposed amount in FIG. 8. As seen in FIG. 8, flare at the peripheral field angle is reduced because of the inserted aperture diaphragm 91. This allows a substantial photographing field angle to be widened.

The above explanation is given to the flare generated when the light shielding plate 90a located in the substantially conjugated position with the crystalline lens posterior surface of the eye E in the optical path of the illumination optical system 10 is changed over to the light shielding plate 90b having a smaller light shielding region in order to photograph the examinee's eye E with a small pupil diameter. However, the light shielding member of the illumination optical system 10 to be changed over to photograph the eye E with a small pupil diameter is not limited to the light shielding member placed in the substantially conjugated position with the crystalline lens posterior surface. In order to appropriately photograph the eye E with a small pupil diameter, it is sufficient if only illumination conditions for a fundus can be changed on an examinee's eye E. For instance, to photograph an examinee's eye E with a small pupil diameter, an image of a light shielding plate may be formed in a substantially conjugated position with a cornea of the eye E in the optical path of the illumination optical system 10.

In the present embodiment, the image 91' of the aperture diaphragm 91 is formed in the crystalline lens to prevent the photographing light beam Lb from overlapping the illumination light beam La within the crystalline lens However, the invention is not limited thereto and it is only necessary to apply a limitation to the photographing light beam between the fundus and the image of the aperture diaphragm (photographing diaphragm) 31 to thereby restrain the occurrence of flare while keeping the photographing field angle. Also, the image 31' of the photographing diaphragm 31 may be placed in a position other than near the pupil. For instance, the image 31' of the photographing diaphragm 31 may be formed in a position between the pupil and the crystalline lens posterior surface of the eye E. The image 91' of the aperture diaphragm 91 may be formed on a more rear side (closer to the fundus) than the formed image 31' and between the image 90b' of the light shielding plate 90b formed inside the crystalline lens and the anterior surface of the crystalline lens. Even when the image 91' of the aperture diaphragm 91 is formed between the fundus and the image 90b' of the light shielding plate 90b so as not to serve as a field diaphragm, a fixed effect can be obtained.

When the aperture diameter of at least one of the photographing diaphragm 31 and the aperture diaphragm 91 is changed, the light beam from the fundus to the photographing diaphragm 31 is changed. Accordingly, for example, even when the aperture diameter of the photographing diaphragm 31 is decreased while the aperture diameter of the aperture diaphragm 91 is fixed, an effect of reducing flare can be produced.

Although the present embodiment shows the example that the light shielding plate 90a and the light shielding plate 90b of the illumination optical system 10 are changed over according to the pupil diameter of the examinee's eye E and, in sync therewith, the aperture diaphragm 91 is selectively inserted in the fundus observing and photographing optical system 30, the invention is not limited thereto. For example, the light shielding plate 90b and the aperture diaphragm 91 may be continuously placed in the optical paths.

In the present embodiment, furthermore, the photographing diaphragm 31 is placed near the perforated mirror 22 and the aperture diaphragm 91 is put between the focusing lens 32 and the image forming lens 33. An alternative is to interchange the aperture diaphragm 91 and the photographing diaphragm 31. Specifically, the aperture diaphragm 91 is placed near the perforated mirror 22 and in a substantially conjugated position with a crystalline lens and the photographing diaphragm 31 is placed behind the focusing lens 32 and in a substantially conjugated position with a pupil. Another alternative is to place the photographing diaphragm 31 and the aperture diaphragm 91 near the perforated mirror 22. In the above embodiment, the photographing diaphragm 31 is placed in a substantially conjugated position with the pupil. As an alternative, the photographing diaphragm 31 may be placed in a substantially conjugated position with the inside of the crystalline lens of the eye E. In this case, similarly, as long as the image 91' of the aperture diaphragm 91 is placed on a side closer to the fundus than the image 31' of the photographing diaphragm 31 in relation to the conjugate relationship with the eye E, the same flare reducing effect as in the above embodiment can be achieved.

Moreover, in the above embodiment, the optical system for placing the aperture diaphragm 91 and the crystalline lens of the eye E in a substantially conjugate relationship is configured as the infinity correction optical system. As an alternative thereto, the aperture diaphragm 91 has only to be moved in sync with an operation of moving the focusing lens 32 according to a diopter of the eye E. In this case, the outer diameter of the aperture diaphragm 91 is preferably changed. With this configuration, the size and the position of the image 91' of the aperture diaphragm 91 produced through the objective lens 25 remains unchanged even after focus adjustment is performed according to the diopter of the examinee's eye E, resulting in the same effect as above.

Figure 9A:
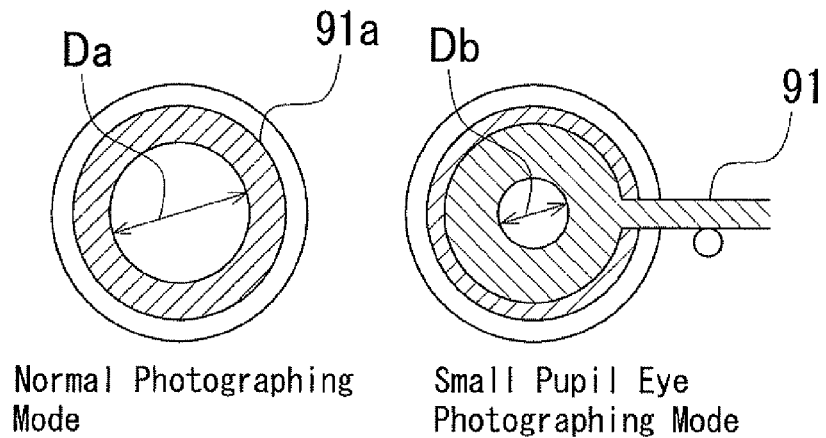
FIGS. 9A to 9C are diagrams showing examples of aperture diaphragms.
Figure 9B:
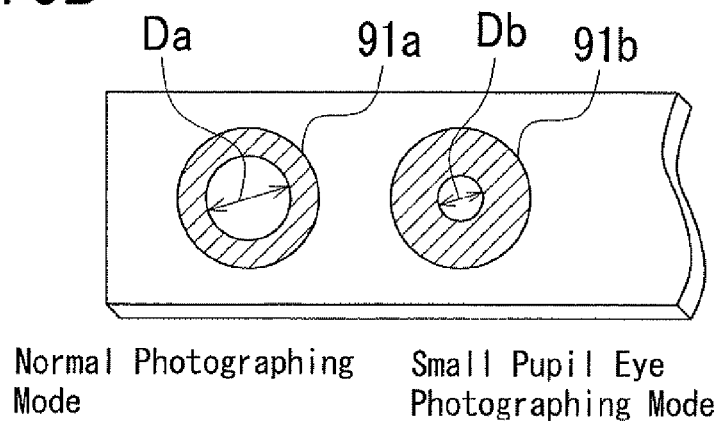
Figure 9C:
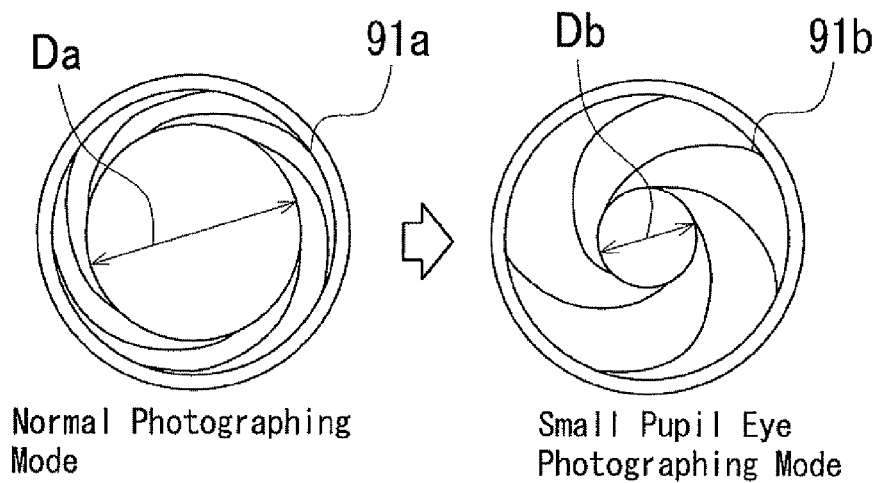

In the above embodiment, the aperture diaphragm 91 is inserted in the optical path as shown in FIG. 9A in sync with changeover from the light shielding plate 90a to the light shielding plate 90b. The invention is not limited thereto and may be arranged as long as an opening state of the aperture diaphragm can be changed according to irradiation conditions of the illumination light to the fundus. For instance, as shown in FIG. 9B, an aperture plate 91a (for normal photographing mode) with an aperture diameter Da and an aperture plate 91b (for small pupil photographing mode) providing the same aperture diameter Db as the aperture diaphragm 91 may be changed over by sliding. Furthermore, as shown in FIG. 9C, another alternative is to use an iris diaphragm having a diaphragm diameter changeable in a stepwise fashion in response to a control signal. In this case, the aperture diameter may be changed from Da to Db in sync with changeover from the light shielding plate 90a to the light shielding plate 90b.

In the above embodiment, a part of the photographing light beam is reduced by insertion of the aperture diaphragm 91. Accordingly, the peripheral portion of the photographed image is likely to be darkened as compared with the central portion. In such a case, a means for correcting illumination unevenness of the photographed image can be used. For instance, it may be arranged so that a concentration distribution filter having a transmission factor different between the central part of light around the optical axis (the light beam) and the peripheral part is appropriately placed in the optical path of the illumination optical system in order to change a distribution of an illumination light amount between the central portion and the peripheral portion of the fundus, so that the fundus is uniformly illuminated by the illumination light through the above filter. For instance, the concentration distribution filter may be attached in a transparent portion of the light shielding plate 90b used in the above embodiment. Accordingly, the concentration distribution filter enables an illumination balance to be different between the center and the periphery of the photographing field angle, thereby uniformizing the illumination light on the fundus. This can prevent the peripheral portion of the photographed image from becoming darkened. The placement of the concentration distribution filter is not limited to the illumination optical system but may be appropriately placed in the optical path of the fundus observing and photographing optical system 30. For instance, the concentration distribution filter is placed in a substantially conjugated position of the fundus observing and photographing optical system 30 with the fundus of the examinee's eye E. Accordingly, the concentration distribution filter can change a balance in light receiving amount between the center and the periphery of the photographing field angle of light incident in the two-dimensional imaging element 35. This can correct unevenness of fundus reflection light caused by non-uniform illumination light to the fundus, thereby preventing the peripheral portion of the photographed image from becoming darkened.

In a case where the light shielding plate 90b is inserted and photographing is conducted, the controller 80 may perform image processing of imaged data (captured image data) outputted from the two-dimensional imaging element 35. This image processing is conduced to correct uneven brightness of the imaged data. For instance, the image processing may include shading correction. By the shading correction, the photographed image at the same level as in the case where the fundus of the eye E is illuminated with uniform brightness can be presented to the examiner. That is when an object (the fundus) having a uniform reflectance in a photographing field angle is photographed, the brightness of the photographed image (gradation values of an image) presented to the examiner is uniform within the photographing field angle. The shading correction is performed, for example, by multiplying the gradation value at each coordinate position of the imaged data (two-dimensional image) outputted from the two-dimensional imaging element 35 by different multiplication coefficients. The plurality of multiplication coefficients are in advance determined by simulation or experiment and stored in the memory 85 in one-by-one correspondence with the coordinates (or portions) of the imaged data. The coefficient values stored in the memory 85 are set for example so that a multiplication coefficient of a peripheral portion of the imaged data is larger than a multiplication coefficient of a central portion.

The controller 80 multiplies the imaged data outputted from the two-dimensional imaging element 35 by the multiplication coefficients stored in the memory 85 to perform the shading correction. The imaged data subjected to the shading correction is stored in the memory 85. The controller 80 causes the monitor 8 to display the imaged data stored in the memory 85. The examiner diagnoses by the image data with reduced illumination non-uniformity displayed on the monitor 8. Although the embodiment shows the shading correction of the imaged data using the multiplication coefficients stored in the memory 85, the invention is not limited thereto. For instance, correcting calculation of the imaged data may be performed by division or by using a lookup table whereby converting the gradation values. In other words, when photographing is performed while the light shielding plate 90b is inserted, the controller 80 is required only to correct the gradation information outputted from the two-dimensional imaging element 35 in order to reduce brightness unevenness of the imaged data caused by non-uniform illumination light to the fundus of the eye E.

As another alternative is to subject the imaged data of the two-dimensional imaging element 35 to a picture image processing by performing gain correction determined from a design value so as to correspond to a field angle of an optical system and increasing a gain in the peripheral portion than in the central portion of the field angle for example so that the brightness is uniform between the central portion and the peripheral portion.

The above embodiment shows the example of reducing flare when the light shielding plate 90a of the illumination optical system is switched over to the light shielding plate 90b to photograph an examinee's eye with a small pupil. A subject to be photographed in the present invention is not limited to an examinee's eye with a small pupil. When an eyeball is turned or moved to change a portion of a fundus to be photographed, a crystalline lens is also turned. This increases the areas caused by overlapping of the illumination light beam La and the photographing light beam Lb as shown in FIG. 7A in the crystalline lens. Thus, flare is more likely to be generated.

Herein, when an examiner changes a lighting position of the light source 74 for guiding a visual line to change a photographing site, on a plane perpendicular to the optical axis, the aperture diameter of the aperture diaphragm 91 (the image 91') is simultaneously changed, so that the overlapping area of the illumination light beam La and the photographing light beam Lb can be reduced. For instance, the aperture diameter of the aperture diaphragm 91 is controlled to be decreased in sync with the time when the lighting position of the light source 74 is changed from a standard lighting position for photographing of a posterior fundus, substantially centered at an intermediate position between a macula and a papilla, to a lighting position for photographing of a papilla, substantially centered at the papilla. Even when a photographing site is the papilla, therefore, a photographed image in which no flare occurs can be obtained as compared with the conventional art.

Herein, it may be arranged to move the aperture diaphragm 91 (the image 91') in a direction perpendicular to the optical axis in sync with the change of the lighting position of the light source 74. For instance, the aperture diaphragm 91 (the image 91') is moved in an opposite direction to a flare generation direction, the photographed image in which no flare occurs can be obtained. Furthermore, the change of the aperture diameter of the aperture diaphragm 91 (the image 91') and the movement of the aperture diaphragm 91 (the image 91') in the direction perpendicular to the optical axis may be combined.

While the presently preferred embodiment of the present invention has been shown and described, it is to be understood that this disclosure is for the purpose of illustration and that various changes and modifications may be made without departing from the scope of the invention as set forth in the appended claims.

REFERENCE SIGNS LIST

10 Illumination optical system
17 Ring slit
18 Relay lens
20 Black point plate
21 Relay lens
22 Perforated mirror
25 Objective lens
30 Fundus observing and photographing optical system
31 Photographing diaphragm
32 Focusing lens
33 Image forming lens
35 Two-dimensional imaging element
90a Light shielding plate (for Normal photographing mode)
90b Light shielding plate (for Small pupil photographing mode)
91 Aperture diaphragm (for Small pupil photographing mode)
92 Image forming lens
93 Field diaphragm

The invention claimed is:

1. A fundus photographing apparatus, comprising:
an illumination optical system for illuminating a fundus of an examinee's eye, the illumination optical system comprising:
a light shielding member provided in the illumination optical system to change over at least two kinds of annular illumination light beams and form a light shielding portion in a substantially conjugated position with a crystalline lens of the eye; and
a photographing optical system for photographing the fundus illuminated by the illumination optical system, the photographing optical system comprising:
a first aperture diaphragm located in a substantially conjugated position with a first position between a pupil and a posterior surface of the crystalline lens of the eye; and
a second aperture diaphragm located in a substantially conjugated position with a second position axially forward of the fundus of the eye between the fundus of the eye and the first position,
wherein the first aperture diaphragm and the second aperture diaphragm are located in the same optical path along which photographing light from the fundus travels in the photographing optical system,
wherein the illumination optical system further comprises a controller configured to change an aperture diameter of at least one of the first aperture diaphragm and the second aperture diaphragm in synchrony with the changeover of the light shielding member.

2. The fundus photographing apparatus according to claim 1, further comprising a focusing lens movable along an optical axis in the optical path of the photographing optical system according to a diopter of the eye,
wherein the second aperture diaphragm is placed in a focus position of the focusing lens, and
the photographing optical system includes an infinity correction optical system formed by the second aperture diaphragm and the focusing lens.

3. The fundus photographing apparatus according to claim 1, wherein one of the illumination optical system and the photographing optical system includes a concentration distribution filter for reducing bright unevenness of a photographed image.

4. The fundus photographing apparatus according to claim 1, further comprising an image processing part for performing shading correction of captured image data generated based on a light receiving signal of an imaging element of the photographing optical system,
wherein the image processing part performs the shading correction of the captured image data by different corrections between a central portion and a peripheral portion of a captured image.

5. The fundus photographing apparatus according to claim 1, wherein the second aperture diaphragm is not a field diaphragm.

6. The fundus photographing apparatus according to claim 1, wherein the first aperture diaphragm and the second aperture diaphragm restrict the photographing light from the fundus.

7. The fundus photographing apparatus according to claim 1, further comprising a perforated mirror through which the photographing light from the fundus passes, the perforated minor located in the same optical path as the first aperture diaphragm and the second aperture diaphragm in the photographing optical system,
wherein the first aperture diaphragm and the second aperture diaphragm are located behind the perforated mirror in a traveling direction of the photographing light from the fundus.

* * * * *